United States Patent [19]

Katsuragi

[11] Patent Number: 5,131,739
[45] Date of Patent: Jul. 21, 1992

[54] OPHTHALMOLOGICAL INSTRUMENT FOR CORNEA CURVATURE AND PRESSURE MEASUREMENT

[75] Inventor: Kenjirou Katsuragi, Tokyo, Japan

[73] Assignee: Kabushiki Kaisha TOPCON, Tokyo, Japan

[21] Appl. No.: 439,402

[22] PCT Filed: Jan. 31, 1989

[86] PCT No.: PCT/JP89/00097
§ 371 Date: Dec. 1, 1989
§ 102(e) Date: Dec. 1, 1989

[87] PCT Pub. No.: WO89/06930
PCT Pub. Date: Aug. 10, 1989

[30] Foreign Application Priority Data

Feb. 1, 1988 [JP] Japan .................... 63-21492

[51] Int. Cl.$^5$ .................... A61B 3/10; A61B 3/00
[52] U.S. Cl. .................... 351/212; 351/247; 128/648
[58] Field of Search .................... 128/645, 646, 648, 652; 351/208, 211, 212, 213, 214, 221, 247

[56] References Cited

U.S. PATENT DOCUMENTS

| | | | |
|---|---|---|---|
| 4,665,923 | 5/1987 | Kobayashi | 128/648 |
| 4,705,045 | 11/1987 | Nishimura | 128/648 |
| 4,779,973 | 10/1988 | Miller et al. | 351/212 |
| 4,817,620 | 4/1989 | Katsuragi et al. | 128/648 |
| 4,834,527 | 5/1989 | Kobayashi | 351/208 |
| 4,902,123 | 2/1990 | Yoder, Jr. | 351/212 |

*Primary Examiner*—Rodney B. Bovernick
*Attorney, Agent, or Firm*—Finnegan, Henderson, Farabow, Garrett & Dunner

[57] ABSTRACT

The present invention relates to an ophthalmological instrument capable of measuring the intraocular pressure of an eye to be tested in an noncontact manner and capable of measuring the radius of curvature of the cornea of the eye, provide a single ophthalmological instrument capable of measuring both the intraocular pressure and the corneal configuration. The instrument includes a noncontact type intraocular measuring means for discharging a fluid toward the cornea of the eye and adapted to measure the intraocular pressure of the eye and means for projecting a predetermined target mark to the cornea of the eye and for receiving a reflected image of said target mark adapted to measure the radius of curvature of the cornea in accordance with the configuration of the corneal reflection image of the target mark, both means being integrally constructed.

10 Claims, 8 Drawing Sheets

OPHTHALMOLOGICAL INSTRUMENT FOR CORNEA CURVATURE AND PRESSURE MEASUREMENT

BACKGROUND OF THE INVENTION

A. Field of the Invention

This invention relates to an ophthalmological instrument capable of measuring intraocular pressure of an eye to be tested and the radius of curvature of the cornea of the eye in a noncontact manner.

B. Description of the Related Art

A tonometer for measuring intraocular pressure of an eye to be tested in a noncontact manner is disclosed in, for example, Japanese Patent Publication No. Sho 54-38437, Japanese Patent Application No. Sho 59-242279, or Japanese Patent Publication No. Sho 62-30768.

The device of Japanese Patent Publication No. Sho 54-38437 is designed such that an air pulse as a fluid is discharged toward the cornea of an eye to be tested in accordance with a known pressure-time function and the applanation state of the cornea is photoelectrically detected to measure a period of time starting from the discharge of an air pulse (sometimes referred to as "air puff") to the applanation of the cornea in order to measure intraocular pressure of the eye.

The device of Japanese Patent Application No. Sho 59-242279 is designed such that an air pulse is discharged to the cornea of the eye to detect pressure of the discharging air pulse, a quantity of reflected light from the cornea is photoelectrically detected with reference to the pressure as a parameter, and the intraocular pressure is determined by such a device when the cornea is transfigured by a predetermined amount.

The device of Japanese Patent Publication No. Sho 62-30768 is designed such that an air current of a predetermined pressure is projected to the cornea, a light flux irradiates the cornea, and the intraocular pressure is measured in accordance with varied quantity of the light flux reflected by the cornea before and after the air current is projected to the cornea.

On the other hand, corneal configuration measuring device for measuring the radius of curvature of the cornea of the eye to be tested, is disclosed in Japanese Patent Application No. Sho 61-102800 and Japanese Patent Application No. Sho 61-310009. The devices disclosed in these publications are designed such that a ring pattern is projected to the cornea of the eye through an objective lens facing the eye, an image thereof reflected by the cornea is received by a two-dimensional detecting element, such as an area CCD, and the radius of curvature of the cornea are measured from the configuration of the pattern.

As seen above, heretofore, the measurement of intraocular pressure of the eye and the measurement of the radius of curvature are separately effected using separate devices such as a noncontact type tonometer (hereinafter referred to as the "tonometer") and a corneal configuration measuring device (hereinafter referred to as the "keratometer").

II. SUMMARY OF THE INVENTION

However, both the tonometer and keratometer require proper alignment between the eye and the device body in order to carry out the respective measurements. Because a long period of time and extensive training are required for performing this alignment operation, it takes much time for an eye inspection involving both types of measurements. Therefore, the burden is increased for both the inspector and the person to be inspected.

Also, in spectacle shops, ophthalmic hospitals and the like, tonometers and keratometers are purchased separately and placed in an eye examination room for the above-mentioned purpose. This becomes not only a burden with respect to expense but also a burden with respect to securing space for eye inspection.

The present invention was accomplished in view of the above-mentioned problems. It is therefore the object of the present invention to provide an ophthalmological instrument which is capable of shortening a period of time and reducing labor required for eye inspection and realizing a space saving advantage and a low expense.

In order to achieve the above-mentioned object, an ophthalmological instrument according to the present invention includes a noncontact type intraocular pressure measuring means for discharging fluid toward the cornea of an eye to be tested in order to transfigure the cornea to measure intraocular pressure of the eye, and means for projecting a predetermined target mark to the cornea of the eye in order to measure the radius of curvature of the cornea in accordance with the configuration of an image of the target mark reflected by the cornea.

As the ophthalmological instrument according to the present invention has both functions for measuring the corneal configuration and the intraocular pressure built in one instrument, the measurement of the corneal configuration of the eye and the measurement of the intraocular pressure thereof can be carried out by using one ophthalmological instrument. Accordingly, the measuring period of time can be shortened. Also, space savings of an eye examination room and an eye inspection room, and a low price of the instrument can be realized.

III. BRIEF DESCRIPTION OF THE DRAWINGS

IV. DESCRIPTION OF THE PREFERRED EMBODIMENTS

A. Optical System

1) Overview

Figure 1:
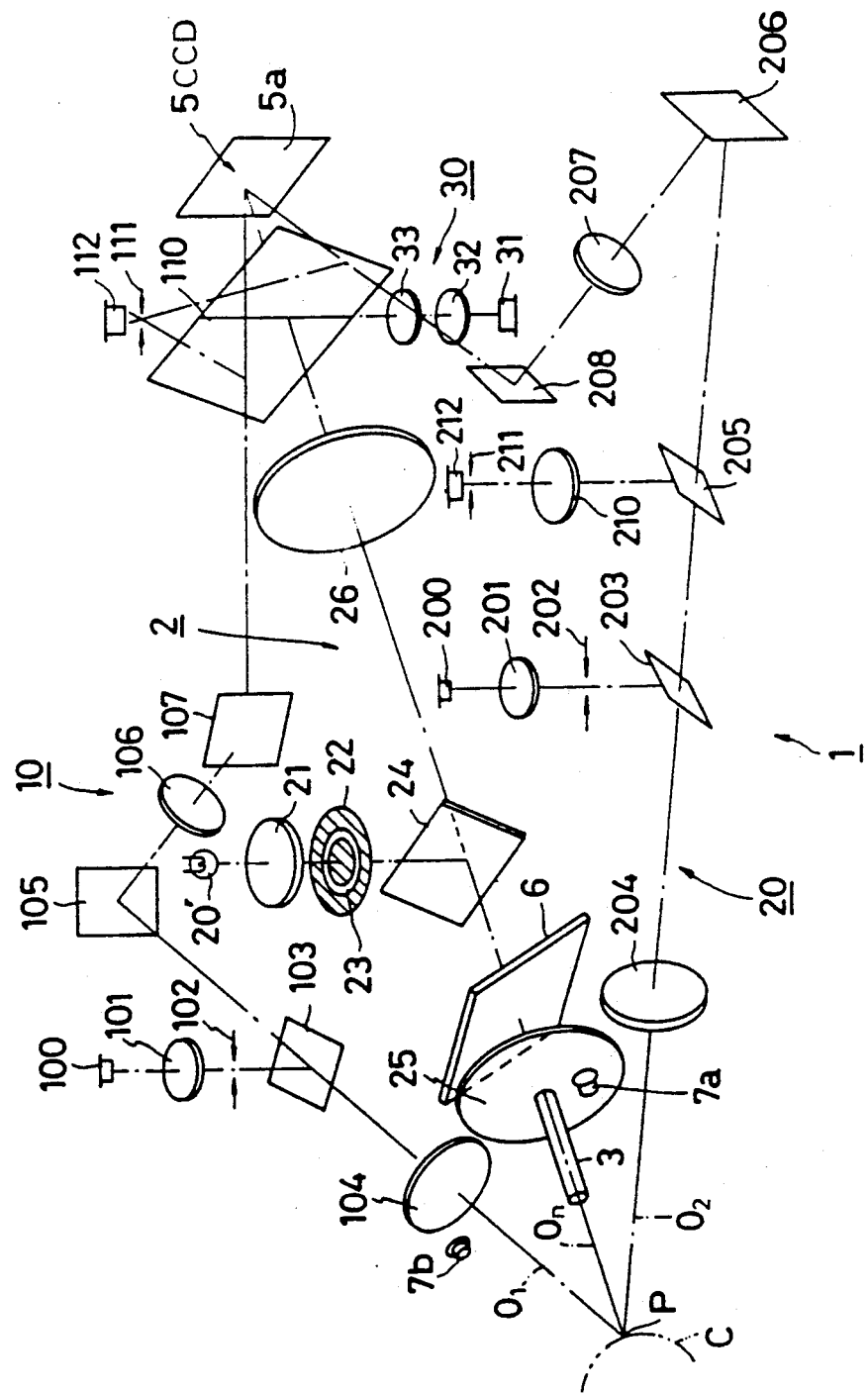
FIG. 1 is a perspective view showing a portion of a measuring system and an optical system according to the present invention.

FIG. 1 shows a perspective view of the constitution of a portion of a measuring system including an optical system of an ophthalmological instrument of the present invention. This measuring system generally comprises an alignment and applanation detecting optical system 1, a corneal configuration measuring and anterior portion observing system 2 having an air puff discharge nozzle 3 as a fluid discharge nozzle, and a reticle optical system 30.

2) Alignment-Applanation Detection Optical System

Figure 2:
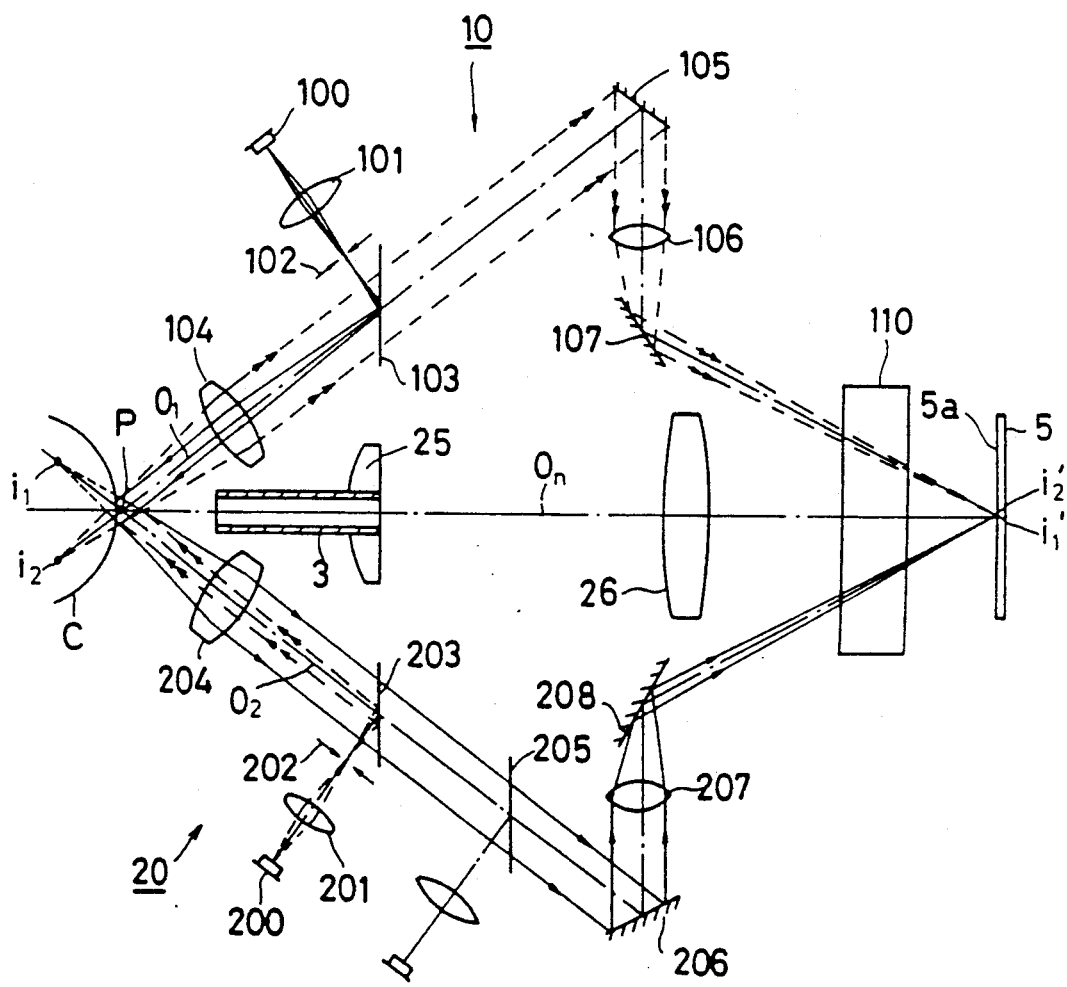
FIG. 2 is an optical diagram of an alignment optical system.

As is shown in FIGS. 1 and 2, the alignment-applanation detecting optical system 1 includes a first optical system 10 and a second optical system 20. The first optical system 10 has an LED 100 as a light source. The LED 100 produces an infrared light of, for example, 760 nm (shown by the solid line in FIG. 2). After condensed by a condenser lens 101, the infrared light of 760 nm is allowed to pass through an aperture 102 as a target mark, reflected by an infrared dichroic mirror 103 and guided to a projection lens 104. The projection lens 104 has a focal point in the position of the aperture 102, and the infrared light of the LED 100 is made into a parallel pencil of rays by the projecting lens 104 and projected to the cornea C of an eye to be tested as a target light. A virtual image $i_1$ as a target image is formed on the cornea C by the target light reflected on the cornea C. The reflected light forming the virtual image $i_1$ becomes a parallel pencil of rays after passed through a projecting lens 204 of the second optical system 20, passes through an infrared dichroic mirror 203 and a half mirror 205 and is guided to an imaging lens 207 between the mirror 206 and the mirror 208 and is then imaged on a light receiving surface 5a of an area CCD 5 as a target image $i_1'$ by the imaging lens 207.

Similarly, the second optical system 20 has an LED 200 as a light source. The LED 200 produces an infrared light of, for example, 860 nm. After condensed by a condenser lens 201, the infrared light of 860 nm is allowed to pass through an aperture 202 as a target mark, reflected by an infrared dichroic mirror 203 and guided to a projection lens 204. The projection lens 204 has a focal point in the position of the aperture 202, and the infrared light of the LED 200 (shown by the broken line in FIG. 2) is made into a parallel pencil of rays by the projecting lens 204 and a virtual image $i_2$ as a target image is formed on the cornea C. The reflected light forming the virtual image $i_2$ becomes a parallel pencil of rays after passing through a projecting lens 104 of the first optical system 10, then passes through an infrared dichroic mirror 103 and is then guided to an imaging lens 106 between the mirror 105 and the mirror 107 and is then imaged on a light receiving surface 5a of the area CCD 5 as a target image $i_2'$ by the imaging lens 106.

When the intersecting point of the respective optical axes $O_1$, $O_2$ (see FIG. 2) of the first and the second optical systems 10 and 20 and the alignment axis On of the air pulse discharge nozzle 3 is made coincident with the vertex P of the cornea C, the virtual images $i_1$ and $i_2$ are present on $O_1$ and $O_2$ and on the focal surface of the cornea C. The target images $i_1'$ and $i_2'$ are there fore made coincident with each other on the light receiving surface 5a of the CCD 5. At this time, a correct alignment between a regular reference operation distance and the eye can be obtained. The light from the imaging lenses 106 and 107 is reflected by a dichroic mirror 110, which permits visual light to transmit and reflects infrared light and which constitutes a part of the corneal configuration measuring and anterior portion observing system 2, and is then made incident to a light receiving element 112 as an alignment sensor through a diaphragm 111.

Also, the reticle optical system 30 generally comprises a light source 31, a reticle plate 32, and an imaging lens 33. The light source 31 emits an infrared light. The infrared light from the light source 31 illuminates the reticle plate 32. The illumination light, which has passed through the reticle plate 32, passes through the imaging lens 33, and is then reflected by the dichroic mirror 110 toward the CCD 5 and imaged on the CCD 5 as a circular reticle image 32a (see FIGS. 11a and 11b) by the imaging lens 33.

Figure 3:
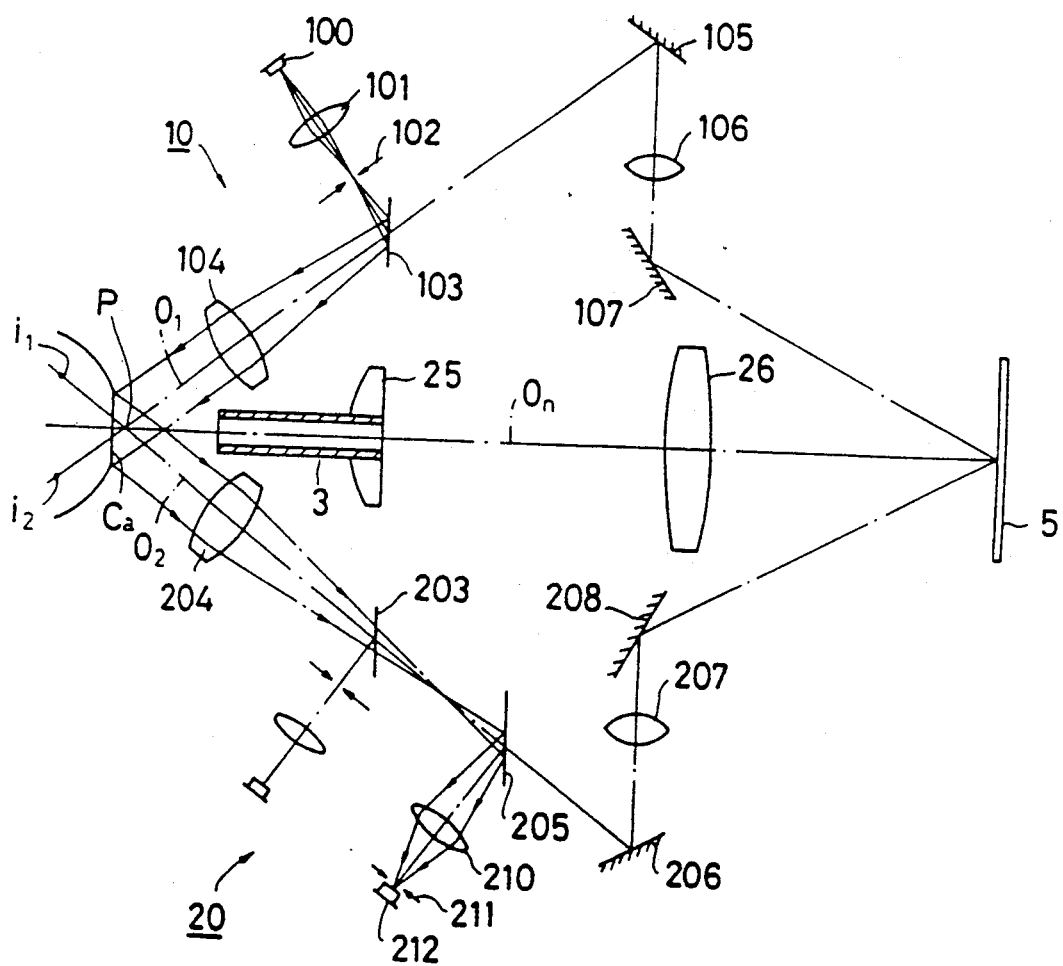
FIG. 3 is an optical diagram of an applanation decting system.

On the other hand, as means for detecting applanation of the cornea, the half mirror 205 of the second optical system, an imaging lens 210, a diaphragm 211, and an applanation detecting sensor 212 are used. As shown in FIG. 3, when an air pulse is discharged from the air puff discharge nozzle 3 to the cornea C and the cornea C is made to applanate, the infrared light from the projecting lens 104 of the first optical system 10 is reflected by the applanated cornea Ca while remaining as a parallel pencil of rays. The light is then made incident to the projecting lens 204 of the second optical system 20, reflected by the half mirror 205 and imaged on an aperture of the diaphragm 211 by the imaging lens 210. The infrared light, which has passed through the aperture 211 is received by the light receiving element 212 functioning as the applanation sensor 212. The light receiving quantity of the light receiving element 212 becomes maximum when the cornea is made applanation.

3) Corneal Configuration Measuring and Anterior Portion Observing System

Figure 4:
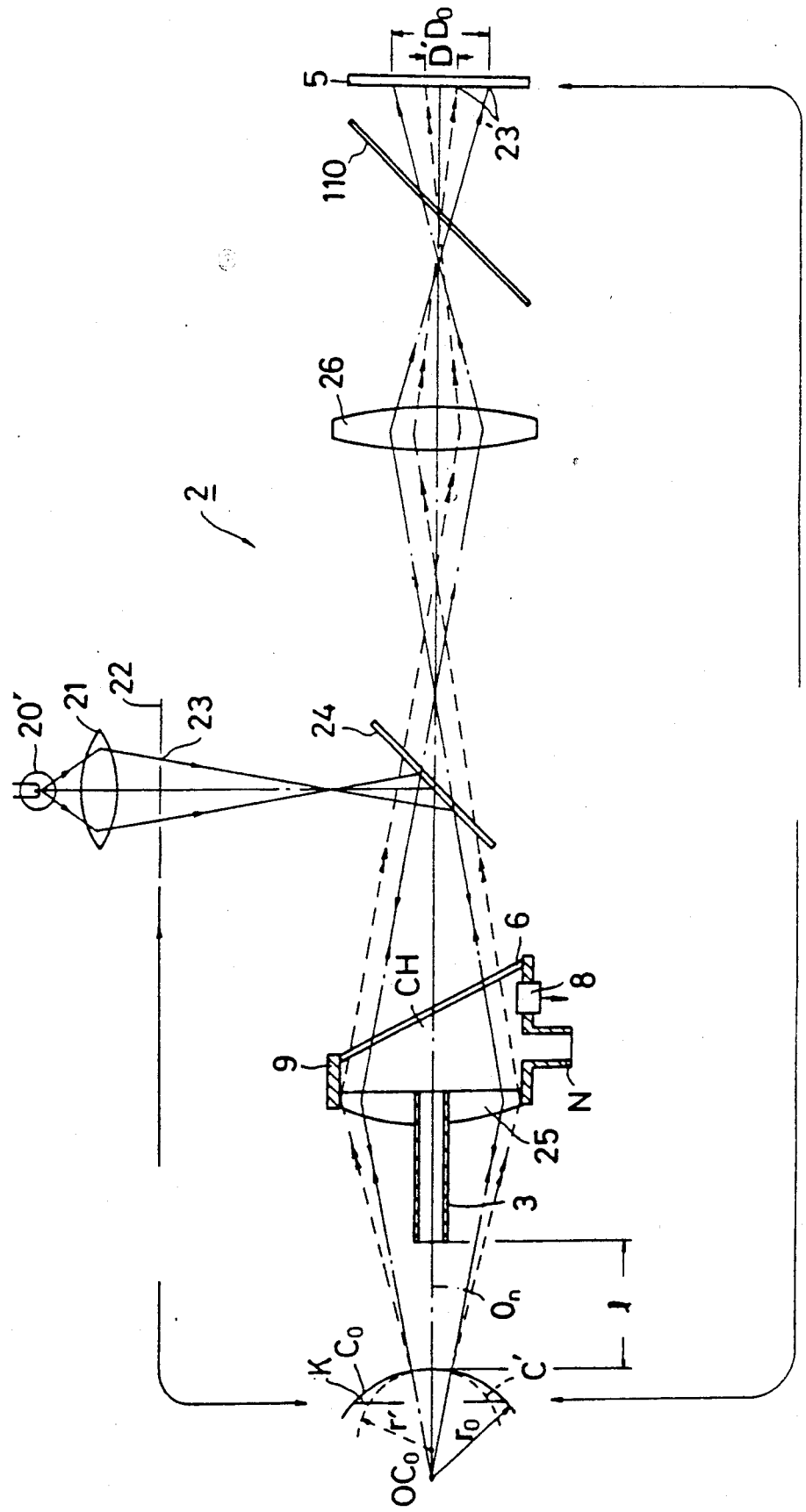
FIG. 4 is an optical diagram of a corneal configuration measuring system.

The corneal configuration measuring and anterior portion observing system 2, as shown in FIG. 4, includes a light source 20', a condenser lens 21, and a pattern plate 22 having a ring-shaped pattern 23 formed thereon, and further includes an anterior portion observing optical system, and an air pulse discharging system which comprise an objective lens, an imaging lens, etc. as will be described hereinafter.

The light source 20' emits a visual light, and the visual light of the light source 20' is condensed by the condenser lens 21 to illuminate the ring-shaped pattern 23 formed on the pattern plate 22. After reflected by the half mirror 24, the light flux, which has passed through the ring-shaped pattern 23, is projected toward the cornea C by the objective lens 25 facing the eye. The objective lens 25 is designed as such that the ring-shaped pattern 23 is formed generally in a position where the iris K is present. The light flux, which has passed through the ring-shaped pattern 23, is projected in such a manner as to be condensed to the center of curvature $OC_o$ of a reference cornea $C_o$. The light flux reflected by the reference cornea $C_o$ is formed on the light receiving surface 5a of the CCD 5 by the objective lens 25 and the imaging lens 26. In this embodiment, the objective lens 25 and the imaging lens 26 are arranged such that the image of the pattern 23 formed in the position of the iris K is optically conjugate with the CCD 5. When the cornea $C_o$ has the radius of curvature $r_o$, if the cornea $C_o$ has no astigmatism, the corneal reflected pattern image 23' to be imaged on the CCD 5 is projected as a ring image of the diameter $D_o$. When the cornea C' has the radius of curvature r' ($r' < r_o$), the corneal reflected image 23' of the ring-shaped pattern 23 is projected as a ring-shaped image having the diameter D'. Therefore, by measureing the size of the pattern image 23' projected on the CCD 5, the radius of curvature of the cornea C can be measured. Also, when the cornea C has astigmatism, the reflected image 23' becomes elliptical and by measuring the long diameter and the short diameter of the ellipse, the radius of curvature in both strong and weak primary meridians of the cornea C can be determined. Furthermore, the axial direction of astigmatism can be determined from the direction of the long or short diameter.

Figure 5:
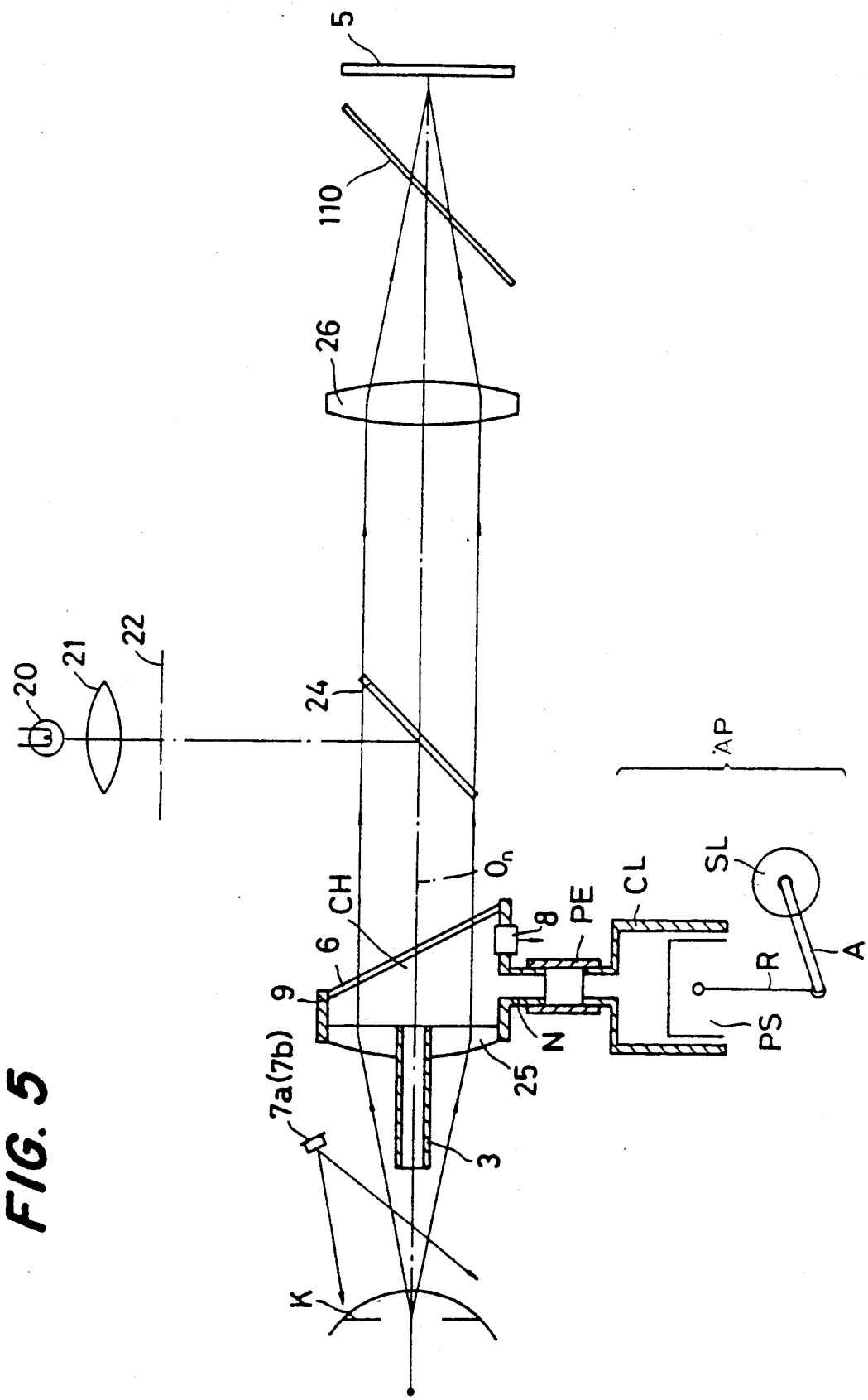
FIG. 5 is an illustration of the anterior portion observing system and an air puff discharge system.

Also, as shown in FIG. 5, the objective lens 25 and the imaging lens 26 to cooperatively constitute the anterior portion observing optical system, and the anterior portion, including the iris K of the eye, is imaged on the CCD 5 as an anterior portion image. The anterior portion is illuminated by visible light 7a, 7b.

B. Air Puff Discharge System

As is shown in FIG. 5, the air puff discharge nozzle 3 of the air puff discharge system is coaxially arranged with the alignment axial line On coaxial with the optical axis of the objective lens 25. The air puff discharge nozzle 3 penetrates the central portion of the objective lens 25 and is mounted in the objective lens 25. The air puff discharge system has an objective lens 25, a glass panel 6 a chamber CH formed in a sealed cylindrical body 9, and an air puff supply system AP comprising a piston-cylinder system. The air puff supply system AP generally comprises a rotary solenoid SL, a crank arm A, a rod R, a piston PS, a cylinder CL, and a pipe PE. The rotary solenoid SL rotates the crank arm A, and the crank arm A moves the piston upward with rod R to compress air within the cylinder CL. The compressed air is fed into the chamber CH through a pipe PE as high pressure air, and the high pressure air within the chamber CH is discharged from the air puff discharge nozzle 3 toward the cornea C of the eye as an air puff. The air puff supply system AP may alternatively comprise a high pressure bomb or spray can and an electromagnetic valve, or otherwise an air compressor and an electromagnetic valve instead of the illustrated piston-cylinder system.

The cylindrical body 9 of the chamber CH is provided with a pressure sensor 8 for measuring air pressure within the chamber CH.

C. Operation of the Measuring Circuit

Figure 6:
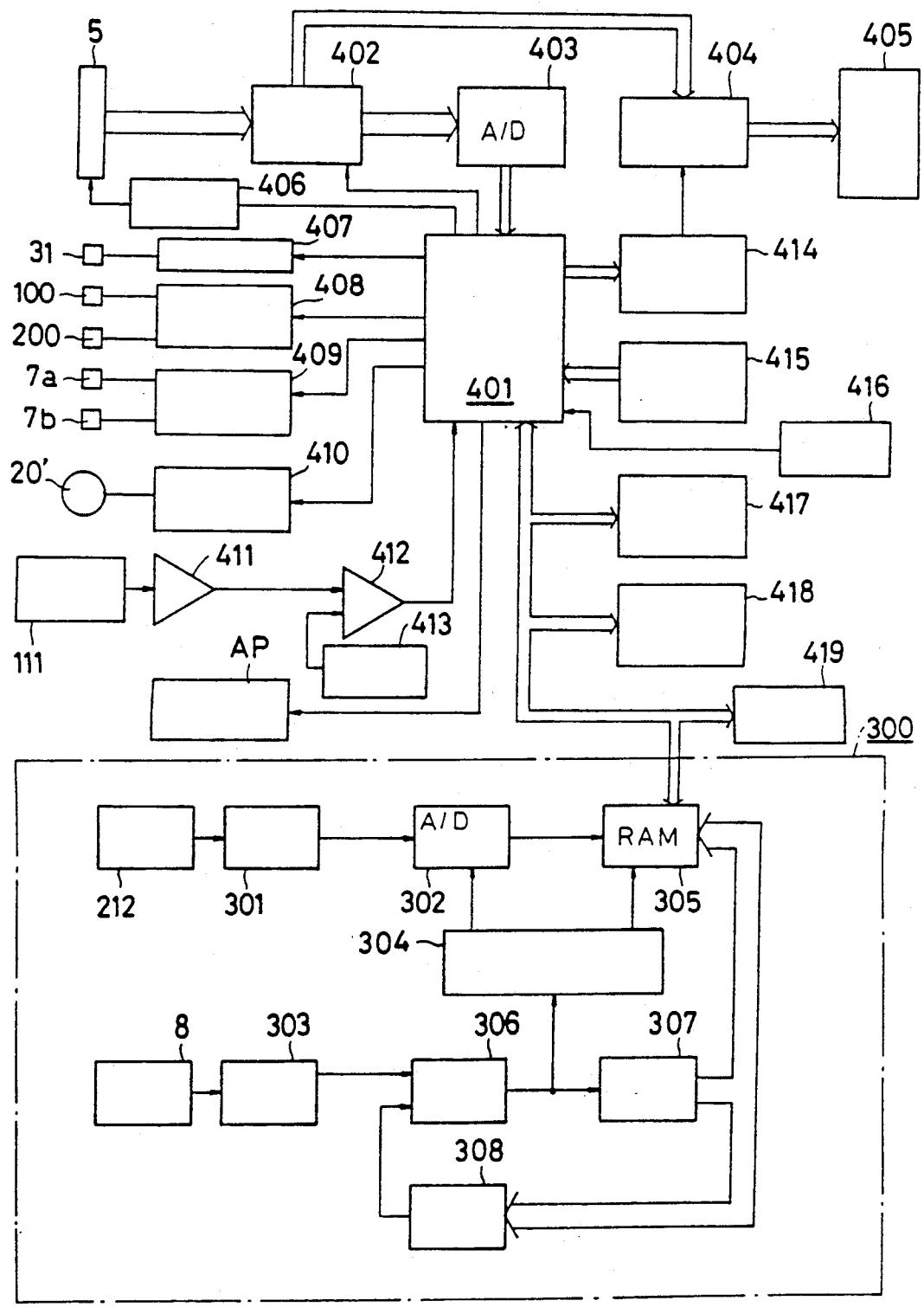
FIG. 6 is a block diagram showing an electric circuit.

FIG. 6 is a block diagram showing the constitution of the measuring circuit. The explanation of this block diagram will be set forth hereinafter together with the measuring steps of the apparatus.

1) Anterior Portion Observation . Alignment Verification Step

When the "auto" mode of a measuring mode changeover switch 416 is selected, a calculation and control circuit circuit 401 lights up the light source 31 through a driver 407 and lights up the light sources 100 and 200 through the driver 408. The light sources 7a and 7b are also lit up simultaneously through the driver 409.

Figure 11A:
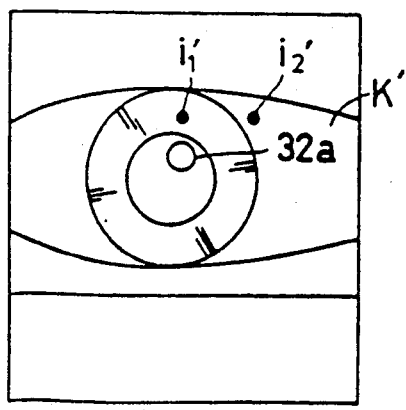

Next, the control circuit 401 actuates the drive circuit 406 to scan the CCD 5. An image receiving signal from the CCD 5 displays an anterior portion image K', the reticle image 32a and alignment target images $i_1'$ and $i_2'$, as shown in FIG. 11a, on a displayer 405 comprising CRT, etc. by a display interface 404.

Figure 11B:
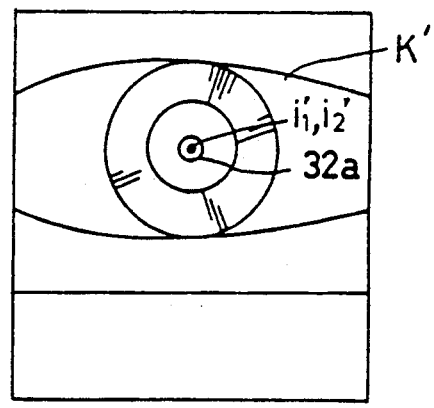

A person, who carries out the measurement, moves a mount (not shown) in the upward and downward, rightward and leftward and forward and backward directions to move the apparatus while looking at the displayed image (FIG. 11a) so that the alignment target images $i_1'$ and $i_2'$ are coincident with each other as shown in FIG. 11b.

By this, the alignment axial line On is coincident with the vertex P of the cornea C and a predetermined working distance l is obtained as shown in FIG. 4.

After amplified by an amplifier 411, the output from the alignment sensor (light receiving element) 111 is compared with the output from a reference value generating circuit 413 by a comparator 412, and the comparator 412 outputs an alignment completion signal to the control circuit 401 when the alignment has been verified as shown in FIG. 11b. The control circuit 401 actuates a character circuit 414 to have the displayer display "alignment OK" through the display interface 404.

2) Pattern Projecting Step for Measuring the Corneal Configuration

Upon receipt of the alignment completion signal, the calculation and control circuit 401 outputs a drive signal to the driver 409, extinguishes the light sources 7a and 7b for the use of illuminating the anterior portion and at the same time drives the driver 410 to light up the light source 20. Also, the calculation and control circuit 401 switches a gate circuit 402 so that output from the CCD 5 would also be input into an A/D converter 403.

Figure 7:
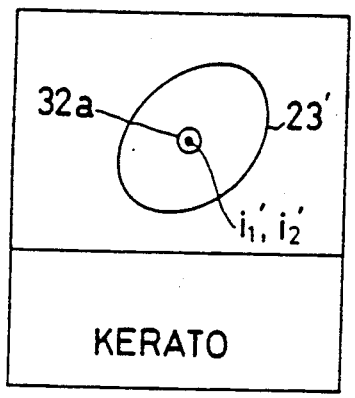
FIG. 7, FIG. 10, FIG. 11a and FIG. 11b are illustrations showing display examples of a displayer.

Also, the calculation and control circuit 401 actuates the character circuit 414 to have the displayer 405 display "KERATO" which signifies that the measurement of the corneal configuration through the display interface 404 has been initiated (see FIG. 7).

Because the anterior portion of the eye is not illuminated by the light sources 7a and 7b, the anterior portion image is not formed on the CCD 5 and therefore the anterior portion image is not formed on the displayer 405. Instead, the light source 20' is lit up and the ring-shaped pattern 23 is projected on the cornea C of the eye and a corneal reflected image of the ring-shaped pattern 23 is formed on the CCD 5 by the objective lens 25 and the imaging lens 26. Accordingly, a ring-shaped pattern 23' is displayed on the displayer 405 (see FIG. 7).

Figure 10:
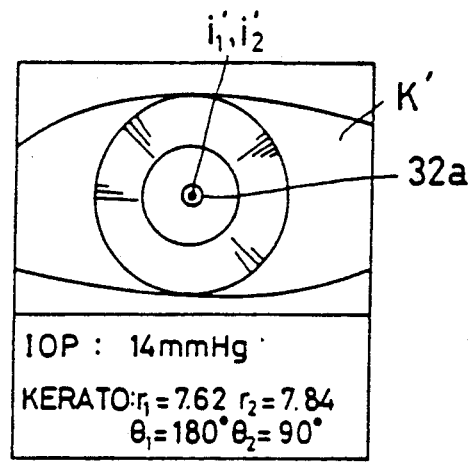

At this time, the image receiving signal from the CCD 5 is input into the A/D converter 403 through the gate circuit 402 to produce a digital signal which is input into a frame memory 417 through the calculation and control circuit 401. The frame memory 417 stores information for one frame portion. The calculation and control circuit 401 extinguishes the light source 20, stops the projection of the ring-shaped pattern, and lights up the light sources 7a and 7b again to illuminate the anterior portion. Also, the gate circuit 402 is switched to stop the input of a received image of the CCD 5 to the A/D converter 403. By this, the anterior portion image K', the reticle image 32a, and the alignment target images $i_1$, $i_2$ are displayed on the displayer 405 as shown in FIG. 10.

3) Intraocular Pressure Measuring Step 300 is a block diagram showing the constitution of a signal processing system of an intraocular measuring system. In this block diagram, reference numeral 302 denotes an A/D converter for converting an applanation signal (corneal reflection light quantity signal) input from the applanation sensor 212 through the amplifier 301 into a digital signal. This A/D converter 302 performs the A/D conversion in accordance with a signal command of a timing controller 304 as will be described hereinafter.

Reference numeral 306 denotes a comparator adapted to compare a pressure signal of the pressure sensor 8 input through the amplifier 303 with a count analog signal obtained by converting a count number of a counter 307 as will be described hereinafter by the D/A converter 308 and output an H-level signal when the pressure signal value is greater than or equal to the count analog signal value and an L-level signal when the pressure signal value is less than the count analog signal value. Reference numeral 304 denotes a timing controller adapted to output a command signal for actuating the A/D converter 302 when the output of the comparator 306 is the H-level and RAM 305 stores the digital signal which has been converted by the A/D converter 302. The counter 307 increases the count number by one whenever the output of the comparator 306 is changed from the L-level to the H-level and designates the addresses of the RAM 305 in sequence in accordance with this count number, and the RAM 305 stores the digital signal converted by the A/D converter 302 in the designated address.

Presuming the counter 307 is set to "0", first, if the voltage of the pressure signal increases sufficiently, the comparator 306 becomes H-level. Then, the count of the counter 307 is incremented to "1". The D/A converter 308 converts the signal corresponding to the "1" output by the counter 307 and outputs the same to the comparator 306 as a count analog signal. The output of the comparator 306 returns to the L-level because the analog count signal has been raised to a higher voltage than the voltage of the pressure signal. At the next machine cycle, the comparator 306 again the count analog signal with the pressure signal. As the voltage of the pressure signal rises in correspondence with the pressure of the air puff, the comparator 306 makes successive low to high transitions, which increment the counter 307 accordingly. In other words, by a loop comprising the comparator 306, the counter 307 and the D/A converter 308, the count number of the count 30 is increased as the pressure of the air puff is raised. Accordingly, the count number corresponding to the pressure of the air puff is output by the counter 307. Also, because the count number designates the address of the RAM 305, the address and the pressure of the air puff correspond to each other.

Next, operation of the intraocular measuring system will be described.

Upon completion of the alignment, the calculation and control circuit 401 discharges an air puff to the cornea C from the air puff discharge nozzle 3.

On the other hand, the pressure sensor 8 outputs a pressure signal corresponding to the pressure of the air puff. The comparator 306 compares this pressure signal with the count analog signal which is output from the D/A converter 308. In this case, as the count number of the counter 307 is reset to zero, the pressure signal value becomes greater than or equal to the count analog signal value. By this, the output of the comparator 306 becomes the H-level from the L-level and the count number of the counter 307 becomes "1". The signal of this count number "1" is converted to a count analog signal by the D/A converter 308 and compared with the pressure signal. At this time, as it is set such that the rising of the output of the D/A converter becomes larger than the pressure rising of the air puff when the count is increased by "1", the count analog signal becomes larger than the pressure signal and the output of the comparator 306 becomes the L-level from the H-level again. The pressure of the air puff is raised with the passage of time and the count number is increased by "1" whenever the pressure signal becomes larger than the count analog signal.

When the cornea C is made to applanate in accordance with the increase in pressure of the air puff as shown in FIG. 3, the applanation signal output from the applanation sensor 212 becomes maximum. Thereafter, as the cornea is brought to be in a concave-shape in accordance with the increase of the pressure, the signal value of the pressure signal is reduced.

Figure 8:
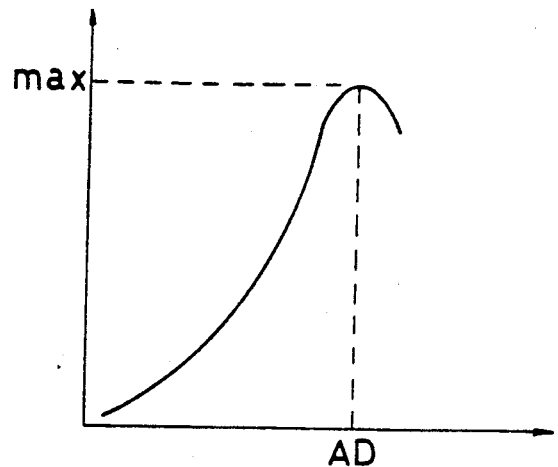
FIG. 8 is an illustration showing a relation between the address of RAM 305 and an applanation signal.

On the other hand, the timing controller 304 outputs a command signal whenever the output of the comparator 306 becomes the H-level and the A/D converter 302 converts the applanation signal output from the applanation sensor 212 into the applanation digital signal whenever the A/D converter 302 receives the command signal. The RAM 305 stores the applanation digital signal in the address designated by the counter 307 as shown in FIG. 8. As this address corresponds to the pressure of the air puff, the address (AD) which stores the maximum value of the applanation digital signal is in correlation with the intraocular pressure of the eye.

4) Corneal Configuration Calculating Step

Figure 9:
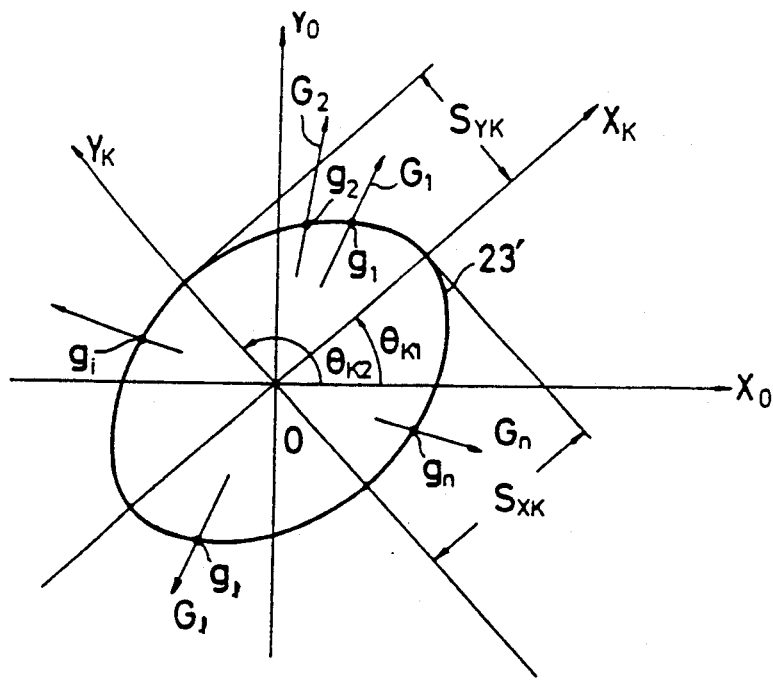
FIG. 9 is an illustration showing a relation between a pattern image and a read scanning line.

Upon completion of storage of data of the RAM 305 of the intraocular pressure measuring system 300, then, the calculation and control circuit 401 reads the image data of the pattern image 23' stored in the scan memory 419 in the corneal configuration measuring pattern projecting step in accordance with memory reading scanning lines $G_1, G_2, \ldots, G_1, \ldots, G_2, \ldots, G_n$ which are stored in the scan memory 419 beforehand. The memory reading scanning lines $G_1, G_2, \ldots, G_1, \ldots, G_2, \ldots, G_n$ scan the data of the frame memory 417 radially about the origin O of the $X_o$-$Y_o$ coordinate as shown in FIG. 9.

The coordinates of points $g_1, g_2, \ldots, g_1, \ldots, g_2, \ldots, g_n$ on the corneal reflection pattern image 23' is obtained.

The calculation and control circuit 401 calculates the elliptical configuration of the pattern image 23' from such obtained coordinate $g_1, g_2, \ldots, g_1, \ldots, g_2, \ldots, g_n$.

The radius $S_{XK}$ of the long axis ($X_K$ axis) of the ellipse 23' corresponds to the radius of curvature $R_1$ of the weak primary meridian of the cornea C, the radius $S_{yk}$ of the short axis ($Y_k$ axis) corresponds to the radius of curvature $R_2$ of the strong primary meridian, and the angle $\theta_{k1}$ of the long axis and the angle $\theta_{k2}$ of the short axis correspond to the axial angle $\theta_1$ of the strong primary meridian and the axial angle $\theta_2$ of the weak primary meridian, respectively.

A general relation of the ellipse 23' in the x-y coordinate is expressed as follows;

$$A_x^2 + B_y^2 + C_{xy} = 1 \tag{1}$$

$$A = \frac{\cos^2\theta_{k1}}{(2S_{xk})^2} + \frac{\sin^2\theta_{k1}}{(2S_{yk})^2}$$

$$B = \frac{\sin^2\theta_{k1}}{(2S_{xk})^2} + \frac{\cos^2\theta_{k1}}{(2S_{yk})^2}$$

$$C = \frac{2\sin\theta_{k1} \cdot \cos\theta_{k1}}{(2S_{xk})^2} + \frac{2\sin\theta_{k1} \cdot \cos\theta_{k1}}{(2S_{yk})^2}$$

Also, given that the radius of the cornea C is r, the radius of the ring-shaped pattern 23 is h, the working distance is l, and the whole power of the projecting optical systems 25 and 26 is $\beta$, the radius $S_k$ of the ring-shaped pattern image 23' has the following relation.

$$S = Y \times \beta$$

$$Y = h \times r/2l$$

Therefore, $S_{xk}$ and $S_{yk}$ are found from the relations (1) and (2), and the radius of curvature $r_1$ of the strong primary meridian can be obtained from the following relation;

$$r_1 = \frac{2S_{xk} \cdot l}{\beta \cdot h} \quad (4)$$

Similarly, the radius of curvature $r_1$ of the strong primary meridian can be obtained from the following relation;

$$r_2 = \frac{2S \cdot l}{\beta \cdot h} \quad (4)'$$

Also, there can be obtained as the strong primary meridian axial angle $\theta_1 = \theta_{k2}$ and the weak primary meridian axial angle $\theta_2 = \theta_1$. Such obtained radii of curvature $r_1$ and $r_2$ and axial angles $\theta_1$ and $\theta_2$ are stored in the data memory 418.

5) Intraocular Pressure Calculating Step

The calculation and control circuit 401 reads the corneal reflection light quantity data which are stored in the RAM 305, compares the various data, finds the address AD where the maximum light quantity $L_{max}$ (see FIG. 8) is stored, calculates the intraocular pressure IOP from the following predetermined intraocular pressure converting formula;

$$IOP = a(AD) + b \quad (5)$$

in accordance with the address value AD, and such obtained IOP value is stored in the data memory 418.

6) Displaying Step

The calculation and control circuit 401 digitally displays the measuring data $r_1$, $r_2$, $\theta_1$, $\theta_2$ and IOP, which are stored in the data memory 418, on the displayer 405 through the character circuit 414 and the display interface 404 as shown in FIG. 10.

The above-mentioned sequential action is run in accordance with a sequence program stored in the memory program 415. As described in the foregoing, when the "AUTO" mode is selected by the measuring mode change-over switch 416, the corneal configuration pattern projection is first run after verification of the alignment, and then it goes to the intraocular pressure measuring step automatically. This ophthalmological instrument is designed such that if the person who carries out the measurement selects only a mode for "corneal configuration measurement" or "intraocular pressure measurement", only the steps corresponding to the selected mode are run after completion of the alignment verification.

I claim:

1. An ophthalmological instrument comprising: noncontact type intraocular pressure measuring means for discharging fluid toward the cornea of an eye to be tested in order to transfigure the cornea to measure intraocular pressure of the eye, said intraocular pressure measuring means having a fluid discharge nozzle adapted to discharge said fluid toward the cornea of the eye; and curvature measuring means for projecting a predetermined target mark to the cornea of the eye in order to measure the radius of curvature of the cornea in accordance with the configuration of an image of the target mark reflected by the cornea, said curvature measuring means having an objective lens facing the eye, wherein said intraocular pressure measuring means includes a first optical system and said curvature measuring means includes a second optical system, said first and second optical systems are common alignment optical systems.

2. An ophthalmological instrument according to claim 1, further comprising:

a first alignment target mark projecting system having an optical axis intersecting an optical axis of said objective lens for projecting a first alignment target light to the cornea of the eye in order to form a first virtual image in accordance with the corneal specular reflection;

a second alignment target mark projecting system having an optical axis symmetrical to the optical axis of said first alignment target mark projecting system with respect to the optical axis of said objective lens for projecting a second alignment target light to the cornea in order to form a second virtual image in accordance with the corneal specular reflection;

a first light receiving optical system adapted to guide said first virtual image to a light receiving portion of said curvature measuring means along a portion of the optical axis of said second alignment target mark projecting system; and a second light receiving optical system adapted to guide said second virtual image to said light receiving portion along a portion of the optical axis of said first alignment target mark projecting system.

3. An ophthalmological instrument according to claim 1, wherein said fluid discharge nozzle penetrates a central portion of said objective lens.

4. An ophthalmological instrument comprising: an anterior portion observing system including an objective lens opposite an eye to be tested and a light receiving portion on which an image of the anterior portion of the eye is formed by said objective lens;

a ring target mark projecting optical system disposed adjacent said anterior portion observing system for projecting a ring target light to form a ring target image on the cornea of the eye in order to measure the radius of curvature; and noncontact type intraocular pressure measuring means including a nozzle for discharging a fluid toward the cornea, and a corneal applanation detecting system for projecting a corneal applanation detecting light toward the cornea, for receiving the reflected corneal applanation detecting light in accordance with a corneal specular reflection, and for measuring an intraocular pressure of the eye based upon the transfiguring of the cornea, said intraocular measuring means having an optical system, wherein said ring target mark projecting optical system and said optical system of said intraocular measuring means are common alignment optical systems.

5. An ophthalmological instrument according to claim 4 further comprising:
- a first alignment target mark projecting system having an optical axis intersecting an optical axis of said objective lens for projecting a first alignment target light to the cornea of the eye in order to form a first virtual image in accordance with the corneal specular reflection;
- a second alignment target mark projecting system having an optical axis symmetrical with the optical axis of said first alignment target mark projecting system with respect to the optical axis of said objective lens for projecting a second alignment target light to the cornea in order to form a second virtual image in accordance with the corneal specular reflection;
- a first light receiving optical system adapted to guide said first virtual image to said light receiving portion along a portion of the optical axis of said second alignment target mark projecting system; and
- a second light receiving optical system adapted to guide said second virtual image to said light receiving portion along a portion of the optical axis of said first alignment target mark projecting system.

6. The ophthalmological instrument of claim 4, wherein said corneal applanation detecting system includes a signal processing system for outputting an electrical signal corresponding to the intraocular pressure.

7. The ophthalmological instrument of claim 6, wherein said signal processing system comprises:
- an applanation sensor for sensing the maximum applanation of the eye and outputting a signal corresponding to said maximum applanation;
- a pressure sensor for sensing the pressure of said fluid and outputting a signal corresponding to said pressure; and
- a storage means for storing in a memory an output value of said applanation sensor at a memory location corresponding to an output value of said pressure sensor.

8. The ophthalmological instrument of claim 7, wherein said storage means comprises:
- a RAM;
- a timing controller for controlling said RAM;
- a comparator;
- a counter connected to said comparator; and
- a D/A converter for connecting said counter to said comparator in a feedback loop.

9. The ophthalmological instrument of claim 4, further comprising display means for displaying the anterior portion of said eye to be tested, the radius of curvature of said eye to be tested, and the intraocular pressure of said eye to be tested.

10. The ophthalmological instrument of claim 4, further comprising a control circuit means for controlling the operation of said anterior portion observing system, said ring target mark projecting system, and said intraocular pressure measuring means.

* * * * *